United States Patent [19]
Schietinger et al.

[11] Patent Number: 5,490,728
[45] Date of Patent: * Feb. 13, 1996

[54] NON-CONTACT OPTICAL TECHNIQUES FOR MEASURING SURFACE CONDITIONS

[75] Inventors: Charles W. Schietinger; Bruce E. Adams, both of Portland, Oreg.

[73] Assignee: Luxtron Corporation, Santa Clara, Calif.

[ * ] Notice: The portion of the term of this patent subsequent to Oct. 13, 2009, has been disclaimed.

[21] Appl. No.: 180,641

[22] Filed: Jan. 12, 1994

Related U.S. Application Data

[60] Division of Ser. No. 999,278, Dec. 28, 1992, Pat. No. 5,310,260, which is a continuation-in-part of Ser. No. 943,927, Sep. 11, 1992, Pat. No. 5,318,362, which is a continuation of Ser. No. 507,605, Apr. 10, 1990, Pat. No. 5,154,512, said Ser. No. 999,278 is a continuation of PCT/US92/03456, Apr. 29, 1991, which is a continuation-in-part of Ser. No. 692,578, Apr. 29, 1991, Pat. No. 5,166,080.

[51] Int. Cl.⁶ ............................. G01B 11/06; G01J 5/06; H01L 21/66
[52] U.S. Cl. ............................ 374/7; 374/121; 374/127; 374/128; 374/133; 364/557
[58] Field of Search ...................... 374/7, 121, 127, 374/128, 133; 364/557

[56] References Cited

U.S. PATENT DOCUMENTS

| | | | |
|---|---|---|---|
| 2,709,367 | 5/1955 | Bohnet | 374/131 |
| 3,288,625 | 11/1966 | Kauer . | |
| 3,586,851 | 6/1971 | Rudolph | 362/268 X |
| 3,686,940 | 8/1972 | Kockott | 250/89 X |
| 3,698,813 | 10/1992 | Aisenberg | 356/48 |
| 3,971,939 | 7/1976 | Andressen | 250/339 |

(List continued on next page.)

FOREIGN PATENT DOCUMENTS

| | | |
|---|---|---|
| 0208067 | 1/1987 | European Pat. Off. . |
| 0380412 | 1/1990 | European Pat. Off. . |
| 57-30916 | 2/1982 | Japan . |
| 2118069 | 10/1988 | Japan . |
| 19944 | 11/1992 | WIPO ................................ 374/121 |

OTHER PUBLICATIONS

Accufiber Application Note, "New Ways to Improve RTP Through Optical Fiber Thermometry", pp. 1–16, Jul. 28, 1989.
"Rapid Thermal Processing: Equipment Issues for High Volume Production Environments", by Stultz, Peaks Systems, Inc., Fremont, California.
"Process Control for a Rapid Optical Annealing System", by Gelpey et al., pp. 199–207.
"Rapid Annealing Using Halogen Lamps", by Kato et al., Suwu Seikosha Co., Ltd., Nagano, Japan, *J. Electrochem. Soc.*, vol. 131, No. 5, pp. 1145–1152, May 1984.
"Will RTP Emerge as the Cinderella Technology of the '90s?", by Singer, Semiconductor International, Mar. 1989.
"Rapid Thermal Processing", Semiconductor International, Mar. 1989.

(List continued on next page.)

*Primary Examiner*—William A. Cuchlinski, Jr.
*Assistant Examiner*—Willie Morris Worth
*Attorney, Agent, or Firm*—Majestic, Parsons, Siebert & Hsue

[57] ABSTRACT

Thermal, optical, physical and chemical characteristics of a substrate (11) surface are determined with non-contact optical techniques that include illuminating (23) the surface with radiation having a ripple intensity characteristic (51), and then measuring the combined intensities (53) of that radiation after modification by the substrate surface and radiation emitted from the surface. Precise determinations of emissivity, reflectivity, temperature, changing surface composition, the existence of any layer formed on the surface and its thickness are all possible from this measurement. They may be made in situ and substantially in real time, thus allowing the measurement to control (39, 41) various processes of treating a substrate surface. This has significant applicability to semiconductor wafer processing and metal processing.

56 Claims, 8 Drawing Sheets

U.S. PATENT DOCUMENTS

| | | | |
|---|---|---|---|
| 4,101,759 | 7/1978 | Anthony et al. | 219/405 X |
| 4,222,663 | 9/1980 | Gebhart et al. | 356/45 |
| 4,236,075 | 11/1980 | Nexo | 250/343 |
| 4,254,455 | 3/1981 | Neal, Jr. | 362/296 |
| 4,408,827 | 10/1983 | Guthrie | 374/131 |
| 4,417,822 | 11/1983 | Stein et al. | 374/129 |
| 4,437,772 | 3/1984 | Samulski | 374/129 |
| 4,540,293 | 9/1985 | Shores | 374/130 |
| 4,576,486 | 3/1986 | Dils | 374/131 |
| 4,579,461 | 4/1986 | Rudolph | 374/9 |
| 4,579,463 | 4/1986 | Rosenowarg | 374/57 |
| 4,632,908 | 12/1986 | Schultz | 374/130 X |
| 4,745,291 | 5/1988 | Niiya | 250/560 |
| 4,750,139 | 6/1988 | Dils | 364/557 |
| 4,752,127 | 6/1988 | Zafred | 250/341 X |
| 4,752,141 | 6/1988 | Sun et al. | 374/161 |
| 4,796,985 | 1/1989 | Onanian | 350/523 |
| 4,799,787 | 1/1989 | Mason | 374/131 X |
| 4,799,788 | 1/1989 | Berthet et al. | 356/45 |
| 4,850,661 | 7/1989 | Kawakatsu | 359/359 |
| 4,865,406 | 12/1989 | Kageyame . | |
| 4,896,928 | 1/1990 | Perilloux | 359/359 |
| 4,919,542 | 4/1990 | Nulman | 374/9 |
| 4,979,134 | 12/1990 | Arima et al. | 364/557 |
| 4,983,001 | 1/1991 | Hagiuda et al. | 359/584 |
| 4,989,970 | 2/1991 | Campbell et al. | 356/73 |
| 5,004,913 | 4/1991 | Kleinerman | 250/227.21 |
| 5,048,960 | 9/1991 | Hayashi et al. | 356/319 |
| 5,154,512 | 10/1992 | Schietinger et al. | 374/9 |
| 5,156,461 | 10/1992 | Moslehi et al. | 374/121 |
| 5,166,080 | 11/1992 | Schietinger et al. | 374/7 X |
| 5,180,226 | 1/1993 | Moslehi | 374/127 |
| 5,255,286 | 10/1993 | Moslehi et al. | 374/121 |
| 5,270,222 | 12/1993 | Moslehi | 437/8 |
| 5,310,260 | 5/1994 | Schietinger et al. | 374/142 |
| 5,318,362 | 6/1994 | Schietinger et al. | 374/142 |

OTHER PUBLICATIONS

"Temperature Control and Temperature Uniformity during Rapid Thermal Processing", by Vandenabeele et al., pp. 185–202.

"Ripple Technique: A Novel Non–Contact Wafer Emissivity and Temperature Method for RTP", by Schietinger et al., Mat. Res. Soc. Symp. Proc., vol. 224, 1991 Materials Research Society.

"In Situ Emissivity Measurements to Probe the Phase Transformations during Rapid Thermal Processing Co Silicidation", by Schreutelkamp et al., Appl. Phys. Lett., vol. 61, No. 19, pp. 2296–2298, Nov. 9, 1992.

"In–Situ Emissivity and Temperature Measurement during Rapid Thermal Processing (RTP)", by Vandenabeele et al., Apr. 1992.

NON-CONTACT OPTICAL TECHNIQUES FOR MEASURING SURFACE CONDITIONS

CROSS-REFERENCE TO RELATED APPLICATIONS

This is a division of application Ser. No. 07/999,278, filed Dec. 28, 1992, now U.S. Pat. No. 5,310,260, which in turn is a continuation-in-part of the following applications:

1) U.S. Ser. No. 07/943,927, filed Sep. 11, 1992, now U.S. Pat. No. 5,318,362, which in turn is a continuation of application Ser. No. 07/507,605, filed Apr. 10, 1990, now U.S. Pat. No. 5,154,512; and 2) International application No. PCT/US92/03456, filed Apr. 27, 1992, which designates the United States for a national patent, which in turn is a continuation-in-part of application Ser. No. 07/692,578, filed Apr. 29, 1991, now U.S. Pat. No. 5,166,080.

The disclosure of each of the foregoing applications and patents is incorporated herein by this reference.

BACKGROUND OF THE INVENTION

This invention is related to techniques of optical measurement of various conditions of solid object surfaces, such as various thermal and physical conditions of a substrate surface.

There are many examples of industrial processes where material in various forms is necessarily heated by various techniques. One example is in heating materials for the purpose of testing them. Another is in the heat treatment of an object. A further example of is found in the semiconductor processing industry. In this latter example, silicon wafers to be processed are positioned within an enclosed chamber where they are heated by some appropriate technique, usually radio frequency or optical radiation. In one form, such a Semiconductor processing chamber is made, at least partially, of an optically transparent material. Lamps outside the chamber direct a large amount of energy through its transparent walls and onto the wafer. The wafer is heated as a result of its absorption of the thermal radiation. Generally, the chamber is formed of a quartz envelope, or of stainless steel with an optical window. The heated wafer is treated by introducing appropriate gases into the chamber which react with the heated surface of the wafer.

These processes require that the temperature of the wafer be maintained within narrow limits in order to obtain good processing results. Therefore, some technique of monitoring the temperature of the wafer is required. One possibility is to contact the wafer with a conventional thermocouple, but this is precluded by poor measurement and contamination considerations when semiconductor wafers are the objects being heated. For other types of objects, such contact measurement techniques most often are precluded because of a number of practical considerations. Use of a thermocouple also often results in substantial errors because of a differing thermal mass, poor thermal contact and a difference in emittance between the thermocouple and the object being heated.

As a result, most optical heating applications use some form of a long wavelength pyrometer. This technique measures the intensity of the radiation of the semiconductor wafer or other optically heated object within a narrow wavelength band. That radiation intensity is then correlated with temperature of the object. In order to avoid errors by the pyrometer receiving heating optical radiation reflected from the object being heated, the wavelength chosen for monitoring by the pyrometer is outside of the emission spectrum of heating lamps. This detected wavelength range is generally made to be significantly longer than the spectrum of the lamps.

There are several disadvantages to such existing pyrometric systems. First, a measurement made at a longer wavelength will have only a portion of the sensitivity of one made at a shorter wavelength. Second, the emissivity of silicon and other materials that are optically heated is dependent upon the temperature and wavelength at which it is measured. Third, economical photodetectors with the highest signal-to-noise ratio are those which respond to the shorter wavelength emissions. Fourth, existing optical pyrometers have a small numerical aperture and thus provide temperature measurements which are also dependent upon the degree of roughness of the object and film growth being measured. Fifth, existing economical pyrometric techniques are slow, a significant disadvantage in a rapid heating system. Sixth, measurements made through a quartz window by a typical pyrometer are subject to error as a result of a significant amount of energy that is emitted by quartz in longer wavelengths to which pyrometers are sensitive.

Therefore, it is a principal object of the present invention to provide an improved pyrometric technique of temperature and/or emissivity measurements that overcomes these shortcomings.

It is also an object of the present invention to provide non-contact techniques for monitoring and/or measuring various optical conditions of surfaces as well as thermal conditions.

There are also numerous processes involving layers of material, typically thin films, where a physical parameter, such as thickness, of the film must be measured. Usually, it is desired that a new film formed on a substrate have a desired thickness within close tolerances. Other applications involve removal of material from a layer in order to form a thin film having a precise thickness. A major application of thin film technology is also found in the manufacturing of integrated circuits, both in silicon semiconductor and gallium arsenide based technology. A typical process of forming integrated circuits in the type of heated chamber discussed above involves the formation of many films and the removal of films. It is necessary in such thin film processes to know at least when the endpoint of the film formation or removal step has been completed. It is also desirable to be able to monitor and control the process in real time by a technique that does not itself interfere with the process.

Therefore, it is also a principal object of the present invention to provide surface monitoring process having a general utility in numerous processes where thin films are utilized, such as in the manufacture of integrated circuits and in the processing of metals.

It is another object of the present invention to provide a technique for measuring the thickness of very thin films with a high degree of accuracy and high resolution.

There are also many occasions where the structure or chemical composition of a surface changes, either by accident or design, such as by its corrosion, oxidation, surface passivation, formation of rust, and the like. Generally, a layer is formed on a surface that is of a different material than that of the original surface but changes can also occur by molecules of the different material diffusing into the surface. An example of an industrial processes where this occurs is in aluminum processing where slag forms on the molten aluminum surface, or where oil is sprayed onto a surface of the aluminum being rolled. In both of these examples, the surface emissivity is unknown and changing.

Accordingly, it is a further object of the present invention to provide a technique for monitoring and measuring surface characteristics under conditions of such changes occurring.

More specifically, it is an object of the present invention to provide a method of correctly measuring a property, such as temperature, by pyrometric means despite changes in surface emissivity which unavoidably results from such surface changes.

SUMMARY OF THE INVENTION

These and other objects are accomplished by the present invention, wherein, briefly and generally, electromagnetic radiation containing an intensity ripple is directed against an object surface of interest, the intensity of which is measured both before and after the radiation has interacted with the surface by reflection or transmission. These intensity measurements are then electronically processed in order to obtain an indication or measurement of a condition of the surface. The intensity of electromagnetic radiation emissions from the surface are also measured. The measurements are accomplished optically, without having to physically contact the surface. The measurement techniques of the present invention may be used with a wide variety of materials and processes.

Many specific characteristics of a surface, or of a layer being formed on a surface, may be monitored or measured by the techniques of the present invention. These characteristics are categorized into four groups for the purpose of this discussion: (1) thermal, such as temperature or emissivity; (2) optical, such as reflectivity; (3) physical, such as layer thickness; and (4) chemical, such as the composition of a layer or surface.

An advantage of the optical/electronic measurement technique of the present invention is that measurement of one or more such surface conditions may be performed in situ as the object surface is naturally changing or is being processed to bring about a desired controlled change. Further, the present invention allows these measurements to be made substantially instantaneously, in real time with the changing surface being monitored. It is thus highly desirable to use these measurements to automatically control the process of changing the surface. This is of particular advantage in integrated circuit processing techniques for monitoring and controlling the formation or removal of thin films where both surface temperature and film thickness are continuously measured and the results used to control the process. It is also of advantage in metal processing, such as during heat treating of a metal, where the emissivity of the surface is changing during the process.

Additional objects, advantages and features of the many aspects of the present invention will become apparent from the following description of its preferred embodiments, which description should be taken in conjunction with the accompanying drawings.

DESCRIPTION OF THE PREFERRED EMBODIMENTS

Although the improvements of the present invention have application to many varied processes involving the monitoring of surface conditions, a first example to be described involves the measurement of the thermal characteristics and thickness of a film being formed or removed as a step in manufacturing integrated circuits on a semiconductor wafer. Although the initial examples deal with silicon semiconductor processes, they are equally applicable to germanium, gallium arsenide and any other process. The resulting films are extremely thin, on the order of tenths of a micron or less, and must have their thicknesses controlled within very narrow limits. The techniques of the present invention are also utilized to measure thermal characteristics of a semiconductor wafer surface during process steps that do not involve forming or removing a film. Further, after the semiconductor processing examples are described, examples of other applications of the techniques, such as in the monitoring and control of metal processing, are given.

Figure 1:
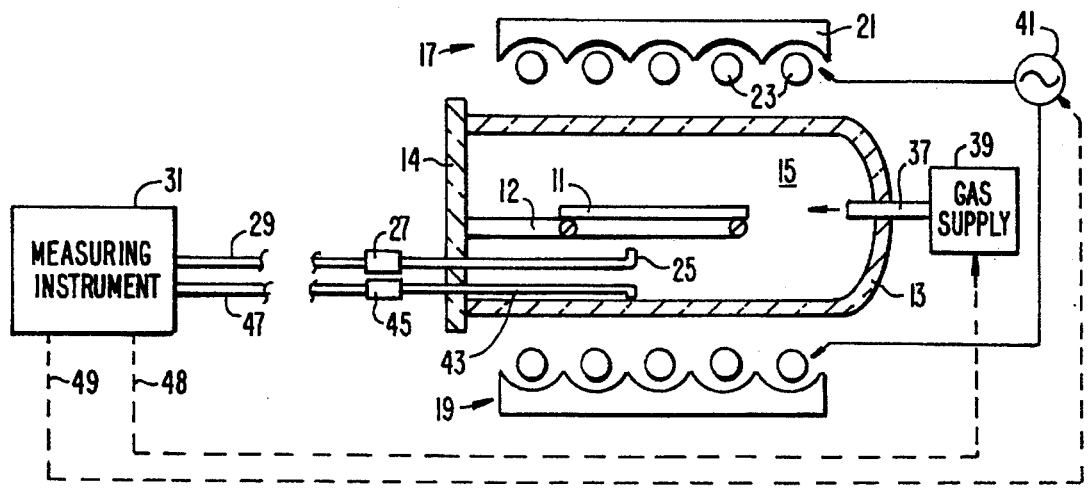
FIG. 1 schematically illustrates a particular type of semiconductor processing furnace that is equipped with a wafer measuring and control system according to the present invention.

Referring to FIG. 1, a silicon semiconductor substrate 11 is positioned within a substantially optically transparent quartz furnace tube 13. The tube 13 and an end plate 14 form an enclosed chamber 15. The substrate 11 is supported by a quartz support 12 attached to the end piece 14, this support allowing most of the bottom surface of the substrate 11 to be exposed. Of course, there are numerous specific silicon wafer support arrangements and heated process chambers that are used in the industry, the support and process chamber of FIG. 1 being generally shown only for the purpose of explaining the film measurement techniques of the present invention.

The type of semiconductor furnace illustrated in FIG. 1 is that which utilizes lamps external to the chamber 15 for heating the wafer 11. Two such banks of lamps 17 and 19 are illustrated, one on either side of the wafer 11. Each has a plurality of quartz lamps, such as the lamps 23 of the light bank 17, and an appropriate reflector, such as a reflector 21. This is, however, but one example of many existing specific configurations of semiconductor furnace heating lamp configurations. The lamps are driven by an alternating current power supply 41. Gasses are introduced into the chamber 15 through an inlet 37 from an appropriate source of gas 39. What has been described so far with respect to FIG. 1 is a general outline of a semiconductor reaction chamber which produces strong background radiation in the range of interest for measurement purposes in which the techniques of the present invention may nonetheless be utilized.

One type of film formed in a semiconductor process is a dielectric film. A typical dielectric is a thin silicon dioxide layer that is grown on either the silicon substrate 11 itself or some other layer of silicon based material, such as polysilicon. It is often extremely important to provide such a silicon dioxide film with the designed thickness within very small tolerances. A particular area of concern is during the formation of gate dielectrics, tunnel dielectrics, and others which are extremely thin.

Accordingly, the techniques of the present invention monitor the emissivity of the substrate surface as the film is formed on it. Since the film, having a different composition, has a different emissivity from that of the underlying substrate, the emissivity measured as a thin film is being formed is a combination of the two when the wavelengths being monitored are in the near infrared portion of the electromagnetic radiation spectrum. The changing composite emissivity is related to the thickness of the film being formed. A light pipe 25 is positioned within the chamber 15 in order to capture radiation emitted from the bottom surface of the substrate 11 on which the film is being formed. This light pipe is made of some material that can withstand the high temperatures occurring within and adjacent the furnace chamber 15, sapphire being one such material. Because of its refractive index, a sapphire light pipe also has a large numerical aperture (angle of acceptance). Cubic zirconia also has these desirable characteristics. Quartz can alternatively be used as a light pipe material. The light pipe 25 is extended a distance away from the chamber 15 to where the temperatures are cooler, and is there coupled by a connector 27 to a more common fused quartz optical fiber 29. That optical fiber is terminated in a measuring instrument 31.

Not only is the desired optical radiation emission of the substrate and forming film being communicated through the light pipe 25 to the measuring instrument 31, the light pipe 25 is also receiving optical radiation within the same infrared or near infrared radiation band from the bank of lights 19. Therefore, a second light pipe 43 is positioned within the chamber 15 and directed to capture intensity of the heating lamps 19 alone, without any direct optical signal from the substrate or film itself. This light signal is coupled by a connector 45 to an optical fiber 47 and thence provided the measuring instrument 31.

The signals in the optical fibers 29 and 47 are detected by the same type of photodetectors within the measuring instrument 31, and within the same wavelength range. The signal from the light pipe 43 is mathematically manipulated with that from the light pipe 25, thus obtaining a signal related to the optical emission of the substrate and film. That signal is then processed in a manner described below to determine the emissivity of the substrate and film. The thickness of the film is then calculated in real time from the emissivity results. These thickness determinations are then preferably used to control the film forming process, such as by adjusting the power of the lamp driving electrical source 41 through a control circuit 49 and controlling the flow or composition of gasses from the gas supply 39 into the chamber 15 by a signal in a control circuit 48. When the endpoint of a film forming process is detected by calculation of the film thickness reaching its desired magnitude, the power source 41 and/or gas supply 39 will be ramped to the end of the process. In the course of the process before reaching endpoint, the thickness measurement is also used to keep the rate at which the film is formed within specified limits by controlling the lamp power and gas supply.

As described below, the emissivity and/or temperature measurements provided by the techniques of the present invention are useful to monitor and or control a wide variety of processes other than the film forming process example being described. The general ability to monitor and/or control temperature of an object being subjected to a wide variety of processes is highly useful. By being able to accurately measure the emissivity of an object surface in real time, various underlying mechanical and chemical changes that are responsible for the variations in the emissivity can be monitored and/or controlled. And, of course, the reflectivity of the surface can also be monitored by the present technique, if desired, and used to control the process. All of these can be measured either in the environment of an optically heated furnace or in other situations where the surface is specially illuminated just for the purpose of making a desired measurement.

Figure 2:
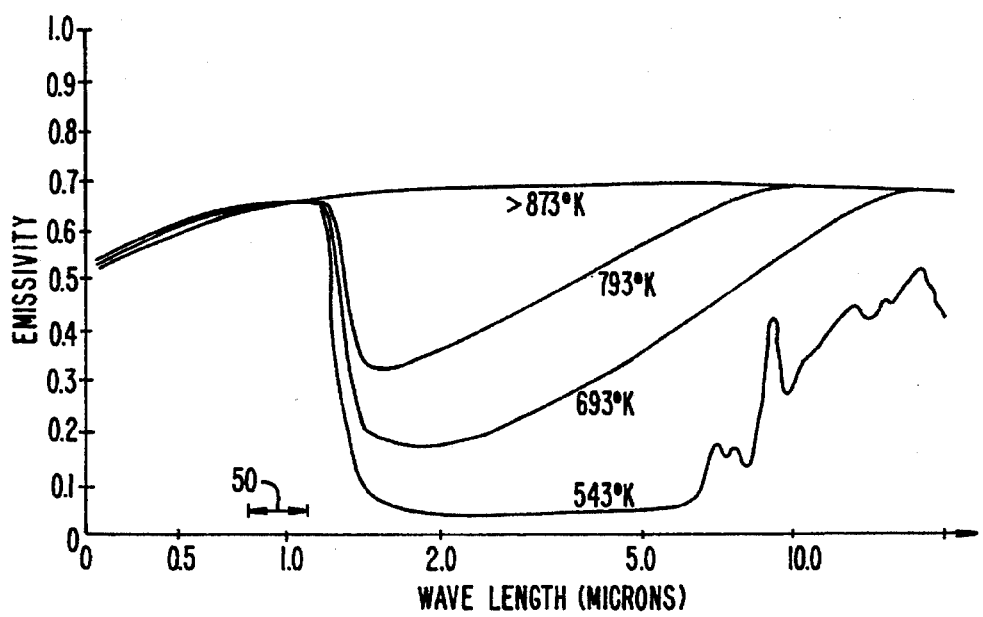
FIG. 2 provides curves that illustrate the emissivity characteristics of one type of substrate upon which a film is controllably formed by the apparatus illustrated in FIG. 1.

Example emissivity characteristics of pure silicon are given in the curves of FIG. 2. A silicon dioxide film being formed on a pure silicon wafer has a different emissivity vs. wavelength characteristic. Since emissivity is also dependent upon the temperature of the substrate and film, a wavelength range of the light pipe 25 optical signal that is detected is preferably that which is the least temperature dependent. Accordingly, a range 50 is illustrated in FIG. 2, extending from about 0.8 to about 1.1 microns, selected to be slightly below the absorption band edge of about 1.2 microns of silicon. As can be seen from FIG. 2, the emissivity of silicon becomes very temperature dependent when observed at wavelengths above that band edge. The detected wavelengths can be limited to the range 50 by positioning an appropriate filter (FIG. 3) in the path of each of the optical signals before reaching its photodetector. Alternatively, a filter can be used that allows all wavelengths below the band gap to be detected, thereby allowing the most light to reach the photodetector but while still excluding those wavelengths above 1.2 microns. Other semiconductor materials have different band gaps, so the wavelength band selected for these measurements will be different, generally slightly below their different band gaps. In the metal processing examples described below, a wavelength range can be chosen which is slightly longer to allow measurements of lower temperatures.

Since temperature cannot totally be eliminated as a variable by wavelength selection, particularly in a general technique used with different combinations of materials, it is usually desired to also measure temperature of a substrate and film from the optical radiation signal therefrom that is captured by the light pipe 25. Both the emissivity and temperature information is then utilized to calculate film thickness. The temperature measurement is also valuable independently of the film thickness measurement, and can be used to control the temperature of the wafer or other sample within the processing chamber or area by controlling the energy supplied to the heating lamps 23 by the power supply 41.

Figure 3:
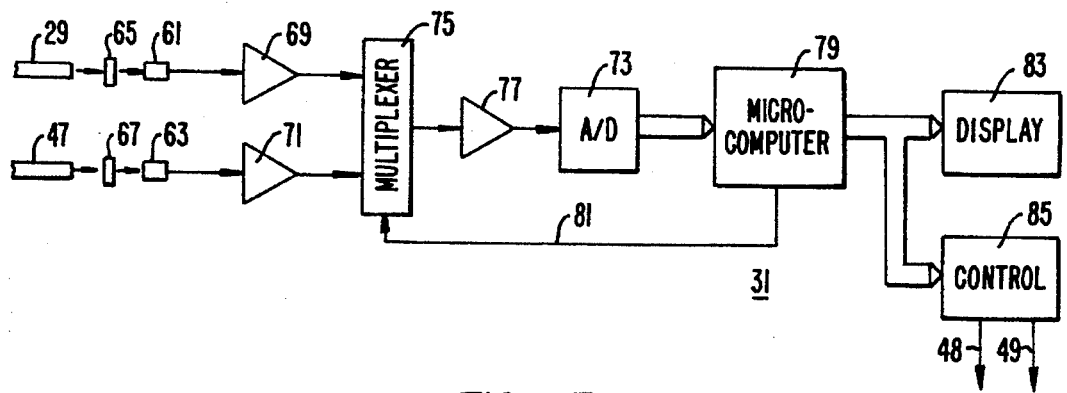
FIG. 3 is a circuit block diagram of the measuring instrument of the apparatus of FIG. 1.

The main functional components of the measuring instrument 31 are illustrated in FIG. 3. A more detailed measuring system for a related application is described in U.S. Pat. No. 4,750,139—Dils (1988). Photodetectors 61 and 63 receive the optical signals from the respective optical fibers 29 and 47. These signals are first passed through optical filters 65 and 67, respectively. These filters preferably pass the same narrow bandwidth 50 (FIG. 2) of optical radiation around 0.95 microns, or all wavelengths below about 1.2 microns, as discussed above, for the specific application being described. The photodetectors 61 and 63 are then preferably a commercially available silicon or indium-gallium-arsenide (InGaAs) type.

The electrical signal outputs of the photodetectors 61 and 63 are amplified by respective linear amplifiers 69 and 71. In order to time share a common analog-to-digital converter 73, a multiplexer circuit 75 is provided to alternately connect the outputs of the amplifiers 69 and 71 to another linear amplifier 77, whose output is then provided as an input to the analog-to-digital converter 73. The digitized signals are received by a microcomputer 79 and processed. The microcomputer 79 can include a very fast digital signal processing (DSP) integrated circuit chip. Part of the controlling function of the microcomputer 79 is to switch the multiplexer 75 by an appropriate control signal in the line 81.

The resulting thickness calculated by the microcomputer 79 from its input signals can either then be displayed on a display device 83 and/or utilized by control circuitry 85 to generate process control signals in the circuits 48 and 49 previously mentioned.

As an alternative to the single photodetector shown in FIG. 3 for each optical channel, a pair of such detectors can be used for each channel. Each of the light pipes 29 and 47 can be coupled into a pair of smaller diameter optical fibers (not shown) that extend to separate photodetectors. One detector of each pair is coupled to a high bandwidth amplifier circuit in order to handle the a.c. ripple without distortion, and the other to a low bandwidth amplifier circuit to carry the average or mean value of the same signal. The multiplexer 75 then has four amplifier outputs as its inputs from which to choose. Part of the signal processing, namely the determination of an average or mean signal, is then carried out by the analog circuitry.

Figure 4:
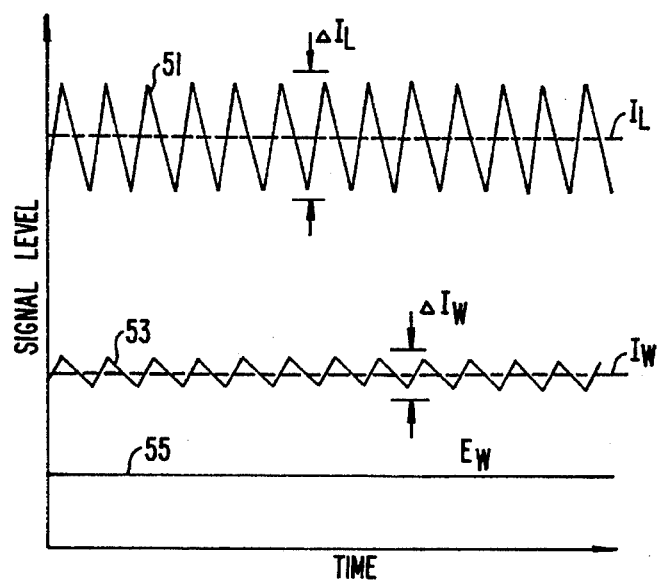
FIG. 4 provides curves to illustrate one specific operation of the apparatus of FIG. 3.
Figure 6:
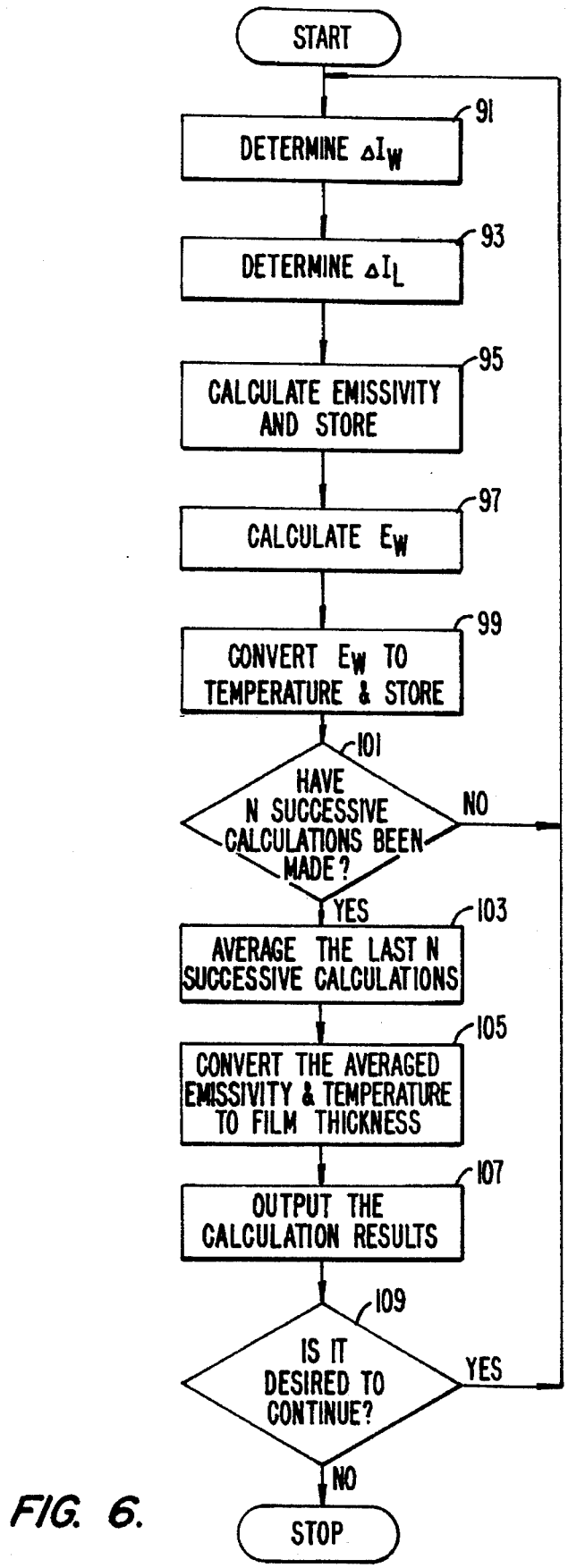
FIG. 6 is a flow chart showing the operation of the micro-computer of the measuring instrument of FIG. 4.

Before describing the calculations performed by the micro-computer 79 with respect to a flow chart of FIG. 6, its processing of the detected optical signals is first illustrated by curves of FIG. 4. A curve 51 shows the signal level output of the detector 63, corresponding to the optical signal of the lamps alone through the light pipe 43. Similarly, a curve 53 illustrates the output of the detector 61 receiving the combined object emission and heating light source reflection received by the light pipe 25. These curves represent the specific example being described since it is not necessary that the light source being used to make the measurements also be used to heat the object. Further, reflectivity and emissivity measurements can be made without detecting the infrared emissions of the object itself.

Each of the signals 51 and 53 contains a ripple (a.c.) component having a frequency of the power source 41 to the heating lamps, generally 60 Hz. in the United States and 50 Hz. in Europe, but no particular frequency is required for making the thickness and/or thermal measurements. A peak-to-peak value of the a.c. component of the signal 51 is indicated by $\Delta I_L$, and that of the a.c. component of the signal 53 is denoted by $\Delta I_W$. The signal levels $I_L$ and $I_W$ represent mean values of the signals 51 and 53, respectively. The peak-to-peak values of these signals, representing a depth of modulation of the signals, are a small proportion of their mean values. The curves of FIG. 4 also show a steady state signal 55 that is proportional to the emission of the heated object 11 ($E_W$) with the effects of lamp radiation reflected from the object having been removed, all being accomplished by the micro-computer processing.

Because the light pipes 25 and 43 are selected to have a very large numerical aperture, the following relationship is true.

$$\text{Wafer Reflectivity} = \rho_o = \frac{\Delta I_W}{\Delta I_L} \qquad (1)$$

Since we also know from Kirchhoff's law that emissivity of an opaque object equals one minus its reflectivity, we can state that:

$$\text{Emissivity} = 1 - \frac{\Delta I_W}{\Delta I_L} \qquad (2)$$

Equation (2) provides a measurement of the emissivity of the object. If its temperature is to be measured, the reflected component of $I_W$ can then be subtracted away, leaving the object emission signal alone, as follows:

$$E_W = I_W - I_L \left( \frac{\Delta I_W}{\Delta I_L} \right) \qquad (3)$$

Thus, the quantity $E_W$ is solely the thermal emission from the object and thus can be converted into temperature of the substrate 11, and the film being formed on it, by Planck's radiation law, in the same manner as with a standard pyrometer. $E_W$ is determined from processing of the d.c. level and a.c. level of the signals 51 and 53.

Further details are provided by the applicants hereof in a paper, Schietinger et al, "Ripple Technique: A Novel Non-Contact Wafer Emissivity and Temperature Method for RTP", *Rapid Thermal and Integrated Processing*, Vol. 224, pp. 23–31, Material Research Society (1991).

Figure 5:
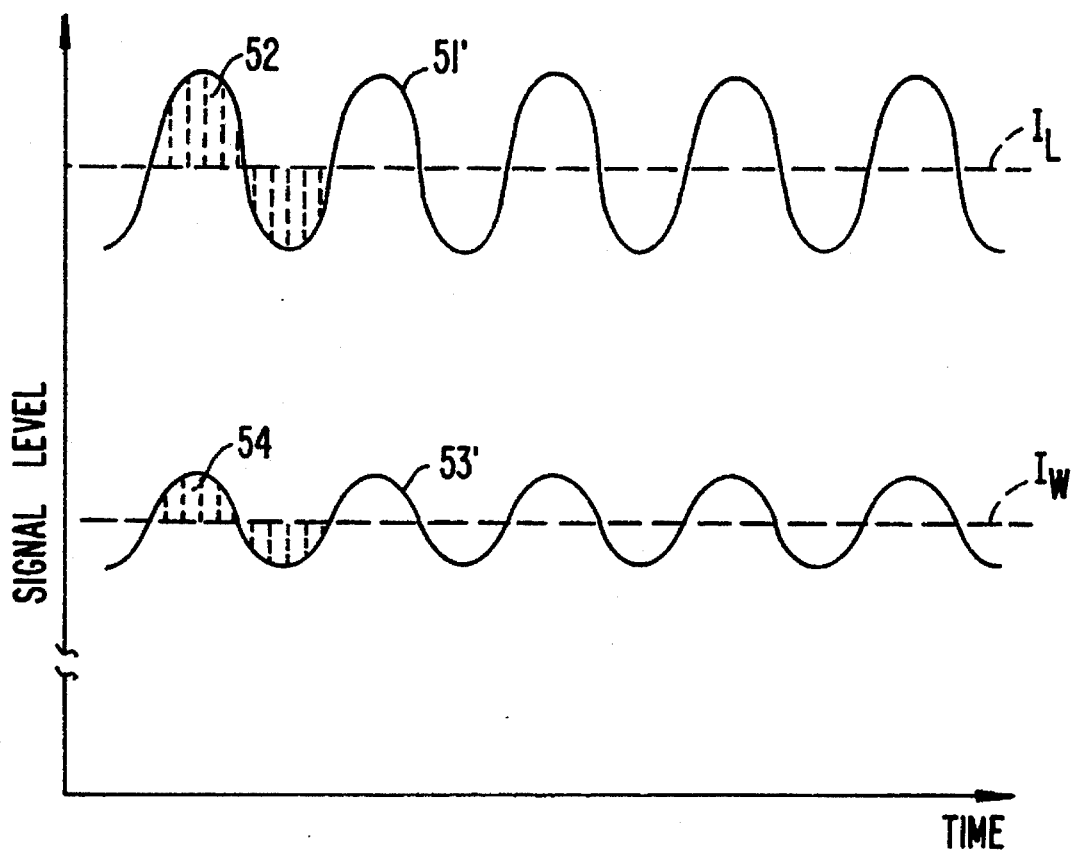
FIG. 5 provides curves to illustrate another specific operation of the apparatus of FIG. 3.

A modified signal measuring technique is illustrated in FIG. 5. Rather than measuring the peak-to-peak values of the lamp signal 51 and the reflected wafer signal 53, as shown in FIG. 4, the microcomputer 79 of the system of FIG. 3 may be programmed to integrate areas 52 and 54 under respective signal curves 51' and 53' with respect to their mean signal values $I_L$ and $I_W$, respectively. That is, the mean values $I_L$ and $I_W$ are first calculated from the digital samples taken of each signal by the system of FIG. 3. An absolute difference in magnitude of each digital sample with its mean signal value is then calculated, and these unsigned differences are accumulated over at least one-half of a signal sample signal cycle but preferably a large number of cycles in order to reduce the effects of any noise that may be present in the signal. These accumulated differences, or areas under the respective curves 51' and 53' then become the $\Delta I_L$ and $\Delta I_W$ quantities used in the subsequent calculations of equations (1), (2) and (3) above. Since the $\Delta I_L$ and $\Delta I_W$ quantities are always ratioed in these equations, it does not matter how many cycles of the respective signals 51' and 53' are integrated to obtain their values so long as data from the same number of cycles is used to calculate each of $\Delta I_L$ and $\Delta I_W$.

As part of this integration technique, it has been found useful to filter the signal outputs of the photodetectors 61 and 63. A narrow bandpass filter around 120 Hz. is used, either in the form of a physical filter in the photodetector analog output signal paths, or as part of the digital processing. The d.c. and near d.c. signal components are then eliminated, making it easier to perform an integration around the mean value of the signals. This also allows the measurement to continue when the power level of the heating lamps is being increased or decreased. The filtering also eliminates unwanted noise outside of the filter bandpass.

Although the detected signals are illustrated in FIG. 5 as sine waves, for simplicity of explanation, they are usually more in the shape of the signals illustrated in FIG. 4. These signals represent the intensity variations of the illuminating lamps which do not generally follow the sine waves of their driving electrical power waveforms. Although accurate results are obtained with the integration technique on such waveforms, an alternate technique is to use an available digital signal processing (DSP) algorithm within the microcomputer 79 instead of using the above mentioned hardware filtering. A suitable algorithm is a finite impulse response filter (FIR). Its use also eliminates a complicating effect that can exist when the heating lamps are driven by three-phase electrical power. In such a case, depending upon the location of the light pipes with respect to the lamps being powered at each of the three phases, the detected signal can include lesser magnitude components shifted in phase with respect to that of the lamps in the immediate vicinity of the light pipes. Whether these other phase signals are of sufficient magnitude to cause a problem or not depends upon a number of factors in addition to the light pipe position, such as the reflective characteristics within the furnace chamber. But if sufficient to cause inaccuracies with the integration technique, use of the DSP algorithm minimizes any adverse effects.

There can be applications where the depth of modulation (proportion of the "ripple" component of the light signals) of the lamp radiation is desirably made to be larger than results from 60 Hz. power being applied to the heating lamps. This can be accomplished, for example, by driving the lamps with a lower frequency a.c. Too low a frequency, however, can have the effect of causing the temperature of the wafer to vary somewhat. As an alternative to a.c. power, a periodically varied or pulsed d.c. can be applied to the lamps at an appropriate frequency. If the depth of modulation (ripple component) of the lamp emission can be controlled in order to be a known value, the light pipe and photodetector that are provided for detecting the lamp radiation could be omitted or simplified.

Referring to FIG. 6, the process of the microcomputer 79 in calculating film thickness is illustrated in the form of a flow chart. Initial steps 91 and 93 determine, respectively, the a.c. component of the detected and digitized signals 53 and 51 of FIG. 4. These a.c. components $\Delta I_L$ and $\Delta I_W$ are determined by one of the three techniques discussed above. A next step 95 is to calculate the emissivity in accordance with Equation (2) above. A next step 97 calculates the steady state quantity 55 of FIG. 4 in accordance with Equation (3) above. That steady state quantity $E_W$ is then converted to temperature of the substrate and film by a reference table or formula empirically determined for the specific substrate and film material compositions being monitored.

At this point, both the emissivity and the temperature of the substrate 11 and film on it have been determined. Since the capabilities of microcomputers allow such calculations to occur at a rapid rate, it is preferable to make the calculations from a large sample of data in quick succession, still within a small fraction of a second, and then average those results before proceeding to calculate the film thickness from them. Thus, a step 101 of the FIG. 6 flow chart keeps track of how many times the emissivity and temperature have been measured and calculated, and will continue to make such calculations until N of them have been made in succession. A step 103 averages the last N calculations.

These averages are then utilized in a step 105 to convert the calculated and averaged emissivity and temperature values into film thickness. This conversion takes place by use of either a table or a formula which has been empirically determined for the particular substrate and film compositions being utilized in the process being monitored. That thickness value is then sent to an appropriate output device by a step 107, such as the display 83 or control circuits 85 of FIG. 3.

So long as the monitoring continues, a step 109 then causes the calculation process to go back to the beginning and again calculate the emissivity and temperature a number N times in succession, calculate film thickness therefrom, and so on. The calculation of thickness by the process of FIG. 6 can easily be made within a fraction of a second utilizing an ordinary type of microcomputer 79, thereby allowing the process illustrated in FIG. 1 to be controlled in real time.

In measurement applications other than film thickness monitoring, the processing step 105 is replaced with a conversion of surface emissivity, usually also with use of a surface temperature determination, into some other desired surface characteristic that varies in some manner related to emissivity. Such other applications include monitoring of various mechanical and chemical characteristics, several examples of which are given herein.

Certain adjustments and corrections in the foregoing calculations have been found to be desirable to improve the accuracy and repeatability of the measurements of the present invention under certain circumstances. The foregoing equations (1), (2) and (3) represent rather ideal circumstances, and more complex versions provide additional precision, when desired, and compensate for differences among semiconductor furnaces or other systems.

It is believed that the results obtained are affected by a number of factors, when present, such as non-uniform light intensity across the source, light entry from the sides of uncovered light pipes, light losses through the light pipe sides, and complex reflections within a chamber in which the substrate is positioned. As a result, some terms are added to the foregoing equations which are set in each case by calibration. Thus, equation (1) above becomes:

$$\rho_{adj} = \frac{\rho_o - k_2}{1 - k_1 \rho_o} \quad (4)$$

where $k_1$ and $k_2$ are coefficients that compensate for reflection and scattering of light within the chamber 15 (FIG. 1). The constant $k_1$ represents an amount of light reflected from the wafer that enters the end or sides of the light pipe 43 pointed toward the lamps, and thus represents an amount of the detected lamp signal $I_L$ which must be subtracted away in order to obtain a signal representative of only the light from the lamps. Similarly, the constant $k_2$ represents an amount of light from the lamps 23 that enters the end or sides of the light pipe 25 without having been reflected from the wafer 11. As a result, equation (2) above for determining emissivity then becomes:

$$\text{Emissivity} = 1 \rho_{adj} \quad (5)$$

Most of the correction, when employed, occurs in the calculation of the surface radiation emission, necessary when measurement of surface temperature is desired. Equation (3) above is modified to include three additional coefficients, as follows:

$$E_{adj} = \frac{I_W - I_L k_2 - \rho_{adj}(I_L - k_1 I_W)}{A + B\rho_{adj} + C\rho_{adj}^2} \quad (6)$$

where the coefficients A, B and C are vectors which represent shape and optical factors and can be temperature dependent. The polynomial of the denominator of equation (6) can be expanded to include higher order terms when the reflectivity of the chamber is low.

These five constants and coefficients are determined for a particular furnace, or other type of system, by calibrating the measuring system. Calibration for use in a semiconductor processing furnace chamber of the type shown in FIG. 1 is described as an example. Either of two calibration procedures may be employed.

A first of the two calibration procedures will now be explained. A first step of this procedure is to calibrate its light pipes and photodetectors in an environment outside of the furnace chamber in order to be able to accurately measure the emissivity of test object surfaces during a second calibration step. In this first step, the radiation emission of a test blackbody is gathered by a light pipe and photodetector from the system being calibrated but outside its furnace chamber. The output of the photodetector is then measured with the blackbody heated to different temperatures by non-optical techniques. The temperature of the blackbody is accurately measured by embedding a thermocouple in it. Since the test blackbody has an emissivity of one, the data gathered of the photodetector output as a function of temperature provides reference data for determining the emissivity of other object surfaces.

As a second calibration step, the emissivity of an object surface of a type likely to be processed in the furnace chamber is accurately measured outside of the furnace, without any heating lamps, by the light pipe and photodetector combination that was calibrated in the first step. A thermocouple is embedded in this object surface as well. It is heated by some appropriate technique that does not affect the optical measurements being made. The emission of the object is measured by the previously calibrated light pipe and detector system at the same temperatures as in the first calibration step. The photodetector outputs in this step will be less than those in the first calibration step because the object surface is not a blackbody. A ratio of the photodetector outputs obtained during the first and second calibration steps at the same temperatures gives the object surface emissivity, if the light pipe and photodetectors are linear. If not linear, some appropriate correction is first made.

As a third step in the calibration procedure, the calibrated light pipe and photodetector system is placed into the semiconductor furnace in which it is to be used. The same substrate that was measured in the second step is also placed into the furnace chamber. The geometric relationship between a substrate holder and the light pipes is maintained the same in the second and third calibration steps, being that used in the furnace chamber after calibration is complete. The temperature of the substrate surface is again accurately monitored by keeping the thermocouple embedded in the substrate. Measurements are then made by the entire system as the substrate is increased in temperature through the various levels where the emissivity of the substrate surface is known from measurements made in the second calibration step. The furnace or other system is operated as it is intended to be operated when the calibrated system is relied upon to make its measurements, including use of its heating lamps to raise the substrate temperature. The emissivity and temperature values calculated from equations (5) and (6) above are then compared with the emissivity measured in the second calibration step and the temperature being measured by the thermocouple. The calculated values will likely be different to some degree from the measured values. It is the purpose of the calibration procedure to adjust the calculations being made to eliminate these differences. After enough such measurements are made, the values of $k_1$, $k_2$, A, B and C of equations (4), (5) and (6) can be mathematically determined which will cause the calculated characteristics of the substrate surface to agree with the measured values, for that particular object surface, with increased precision compared to operating the system without this calibration being done.

Such a calibration is accurate only for one specific substrate surface, however. In order to calibrate the system more completely, steps two and three above are repeated for a number of different types of substrate surfaces. Enough data is then obtained to fix each of $k_1$, $k_2$, A, B and C at single values that will provide accurate results by use of equations (4), (5) and (6) for a wide range of substrate surfaces. Additionally, it may be desirable to add another calibration step where all the measurements described above in step three are made within the chamber but with the heating lamps off, some non-optical means being used to heat the substrate for the purpose of making another set of calibration measurements.

The second, alternate calibration procedure is simpler for the operator to perform since it utilizes a known processing algorithm to determine the values of the five constants that give the best results. In this procedure, a wafer of the type to be processed is positioned in the furnace and an accurate conventional temperature measuring sensor, such as a thermocouple, is attached to the wafer on a side opposite to that from which reflected light is being monitored. The wafer is then stepped through various temperatures levels within an expected actual operating temperature range. The temperature is measured at each level by both the optical technique described above, utilizing equations (4), (5) and (6), and by the thermocouple. An available computer program utilizing the known simplex algorithm (dr other suitable minimization algorithm) is then employed to process all the data in order to determine the values of $k_1$, $k_2$, A, B and C which cause the temperatures calculated by the use of equations (4), (5) and (6) to be the closest to those measured by the thermocouple. These five constants then become the calibrated values used for actual optical temperature and emissivity measurements performed as described above, without any necessity for a thermocouple or other wafer contacting temperature measuring sensor.

Figure 7:
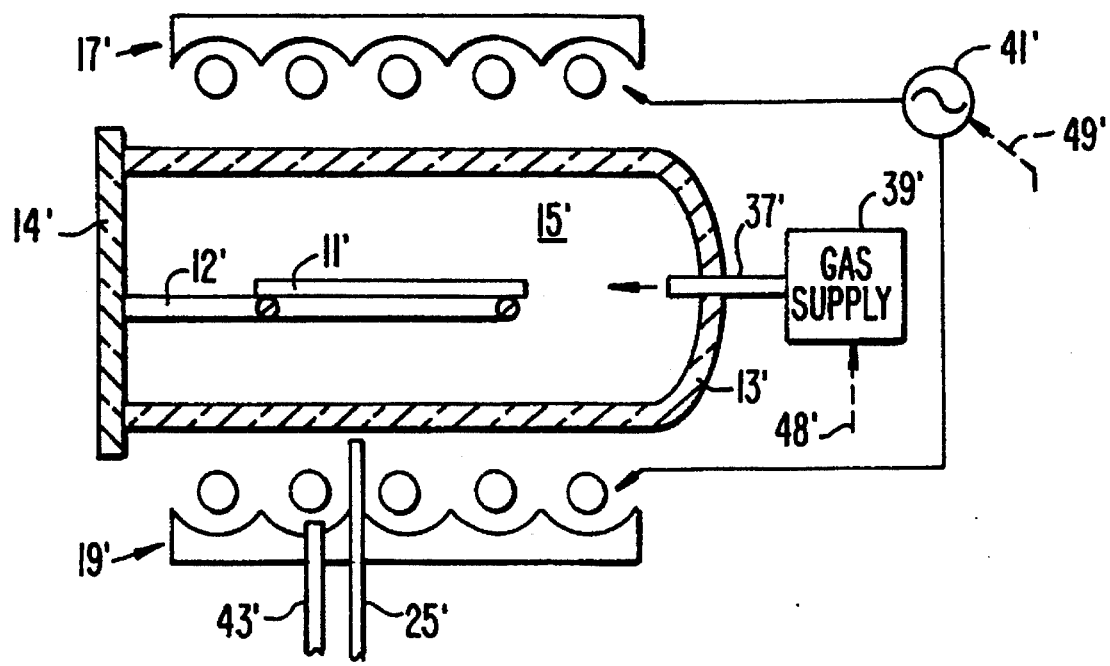
FIG. 7 shows a modified version of the semiconductor processing furnace and measuring system of FIG. 1.

A modification of the system of FIG. 1 is illustrated in FIG. 7, where corresponding elements and components are identified by the same reference numbers but with a prime (') added. The primary difference is the positioning of light pipes 25' and 43' on the outside of the quartz furnace tube 13'. Thus, the light pipe 25' receives emissions and reflected radiation from the substrate 11' through a wall of the tube 13'. The light pipe 43' receives radiation from an optical lamp without any component from within the furnace tube 13'. The difference in the FIG. 7 arrangement is that the optical signals thus detected are somewhat different than those detected within the chamber 15' by the embodiment of FIG. 1, that difference being a filtering effect caused by the quartz or other material used to make the tube 13'.

The example semiconductor processing furnace systems of FIGS. 1 and 7 are of a type utilizing lamps to heat the semiconductor wafers within the processing chamber to the required temperatures where the necessary chemical reactions can take place. This is convenient for application of the techniques of the present invention since a necessary a.c.

driven light source already exists. However, there are different techniques for heating semiconductor wafers, such as using a radio frequency generator or resistance heating, where the light source is not available for use in deriving data necessary to make a reflectivity, emissivity, temperature or film thickness calculation. Further, in fields other than in integrated circuit processing, such heating lamps are likely not utilized. In such circumstances, therefore, it is necessary to direct optical radiation against the substrate surface on which a film is being formed or an unknown emissivity is being measured.

Figure 8:
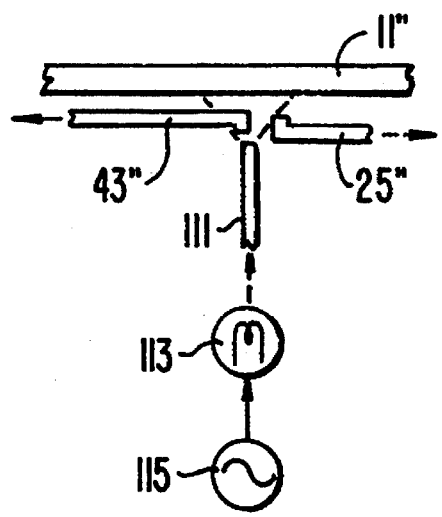
FIG. 8 shows another modification of the FIG. 1 system.

Such a system is schematically illustrated in FIG. 8. An additional sapphire light pipe 111 carries to the subject surface of a substrate 11" optical radiation from a light source 113 that is energized by an alternating current source 115 of any convenient frequency. Alternatively, the light source 113 may be powered by pulsed direct current. It may be desired in certain applications to choose a frequency that is distinct from any ambient light having an alternating intensity component. On the other hand, general building lighting, available from either fluorescent or incandescent sources that are permanently installed, may be used in place of the dedicated light source 113 and light pipe 111 when the application permits. The reflected radiation and emissions from the substrate and film are than gathered by the light pipe 25", corresponding to the light pipe 25 of FIG. 1, and a signal proportional to the intensity of the light striking the substrate 11" is captured by the light pipe 43" corresponding to the light pipe 43 of FIG. 1. Such a system is made practical with the large numerical aperture of the preferred sapphire light pipes.

The wide angle of acceptance of such light pipes results in collecting light that has passed through the film at various different angles, thus traveling through the film with a range of different path lengths. Any variation in intensity level of light passing through the film along any one path that is due to interference effects within the film as it increases in thickness will be different than those variations of light traveling in another path. When all these rays are directed onto a single detector, an averaged signal results which minimizes such interference effects on the emissivity being measured.

Another way to minimize such interference effects is to separately detect in two wavelength bands light passing through the film with a reduced range of angles, such as by directing only central rays of a light pipe onto a photodetector. In the silicon substrate example given above, the second wavelength range would also be less than the 1.2 micron band edge and separated significantly in wavelength from the first range. The bands are kept separate by appropriate beam splitting and filtering with a single pair of light pipes as illustrated herein, or can alternatively utilize an additional pair of light pipes having filters which select the second wavelength band. Also, because of the narrow angle of optical acceptance which is necessary, a traditional optical system, such as a pyrometer, may be substituted for the light pipe.

Yet another way to minimize such interference effects within the film is to separately detect the light passing through the film in at least two different angles with respect to its surface. This can be accomplished by using the large numerical aperture light pipe discussed above but then optically directing its central and outer modes onto different photodetectors. Alternatively, rather than such using a light pipe, two traditional pyrometers may be utilized by directing them at different angles toward the same spot on the substrate surface upon which the film is being formed.

With reference to FIGS. 9, 10A, 10B and 10C, light pipe structures are shown which increase and control the aperture of one or both of the electromagnetic radiation gathering light pipes in the systems shown in FIGS. 1, 7 or 8. The already wide angle of acceptance of the light pipe, brought about by its high refractive index, is more fully utilized by shaping its end to include a lens element. The usual light pipe end, which is planar in a direction perpendicular to a longitudinal axis of the light pipe, is reshaped to provide a domed, convex surface that increases the effective field of view of the light pipe, when coupled into another optical fiber having a much lesser index of refraction and angle of acceptance, without having to provide a separate optical system.

Such a modification is particularly preferred for the light pipe 43 that is used to gather radiation from the heat lamps in the system of FIG. 1, or in different situations where other lamps are used that do not heat the object. It has been found to be desirable to gather the reference light signal through the light pipe 43 over approximately the same area of the light source that is illuminating the portion of the wafer 11 supplying reflected light into the light pipe 25. The wider aperture also gathers more light reflected from internal surfaces of the chamber 15, important because the portion of the wafer being viewed through the light pipe 25 is also illuminated by these reflections.

Figure 9:
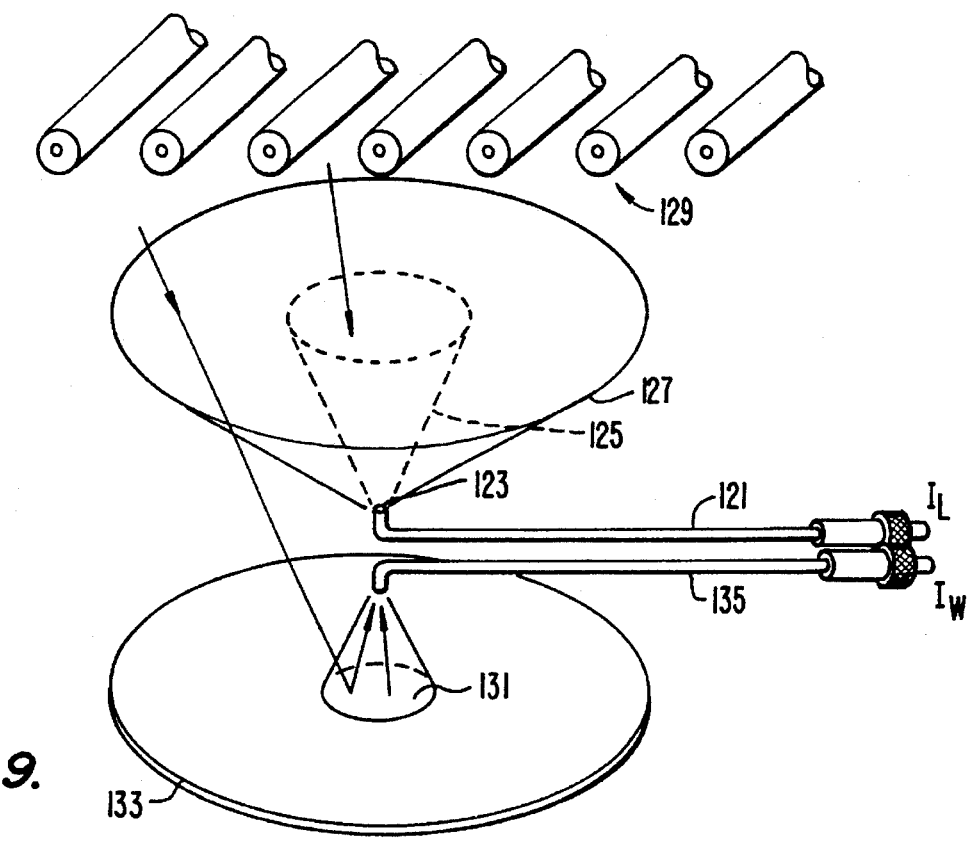
FIG. 9 illustrates desired characteristics of the light pipes used in any of the systems of FIGS. 1, 7 or 8.

FIG. 9 illustrates such a modified light pipe 121 having an approximately spherically shaped convex surface 123 at its light gathering end. FIG. 10B shows an expanded view of this light pipe. A cone 125, shown in FIG. 9 in dotted outline, indicates a field of view of a light pipe with a planar end, in order to provide a comparison with an increased field of view, indicated by the cone 127, that results from shaping the light pipe end into a dome 123. Radiation from heating lamps 129 is then gathered over a larger portion of a lamp area that is irradiating a portion 131 of a wafer 133 from which a second light pipe 135 receives reflected light. The second light pipe 135 corresponds to the light pipe 25 of the FIG. 1 system.

Figure 10A:
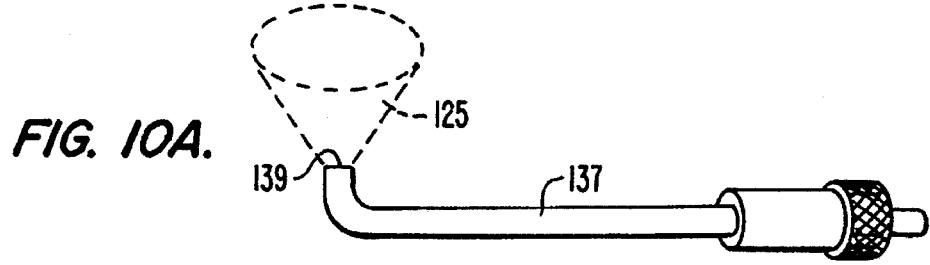
FIGS. 10A, 10B and 10C illustrate three variations in the shape of an end of the light pipes used in any of the systems of FIGS. 1, 7 or 8.
Figure 10B:
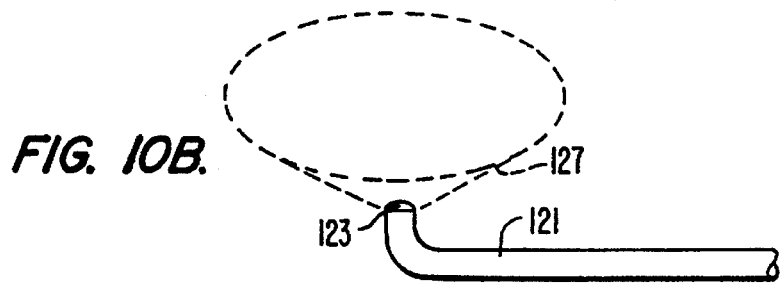
Figure 10C:
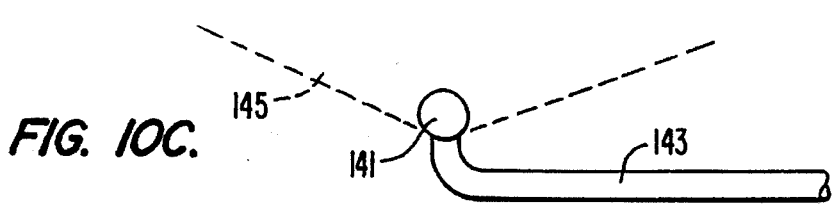

FIG. 10A illustrates the relative size of the cone 125 that represents an effective field of view of a typical light pipe 137 with a planar end 139, when coupled into an optical fiber having a lesser field of view. This can be compared with the cone 127 of the improved light pipe end 123 shown in FIG. 10B. The domed end 123 may be formed from a planar end of a light pipe by either mechanically or flame polishing the end. The material preferred for the improved light pipes remains the high refractive index, high melting point materials previously mentioned, namely sapphire, cubic zirconia or quartz. A further alternative modification is given in FIG. 10C, where an end 141 of a light pipe 143 is formed into ball shape to even further increase its effective field of view 145.

Another technique for increasing the field of view of the light pipes is to properly couple each of them optically to their respective optical fibers. Referring to FIG. 1, as an example, the light pipes 25 and 43, having a very high index of refraction, are coupled into respective quartz optical fibers 29 and 47, having a lower index of refraction, by couplers 27 and 45. Because of the much different indices of refraction, the angle of acceptance of the optical fiber is much less than that of the light pipe to which it is coupled. The result is that not all the light captured by the light pipe is coupled into its respective optical fiber. In order to overcome this, an optical element or a simple optical system is provided as part of each of the couplers 27 and 45 to couple as much of the light intensity as possible from the light pipe into the optical fiber. One embodiment of this is a lens that images the light output of the light pipe into the optical fiber. Alternatively, a diffuser or mode mixer can be employed.

Figure 11A:
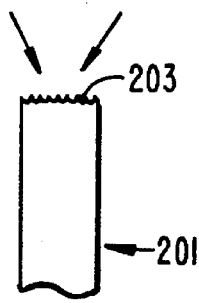
FIGS. 11A, 11B and 11C show alternate light pipe structures for use in any of the systems of FIGS. 1, 7 or 8.
Figure 11B:
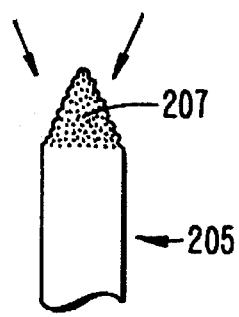
Figure 11C:
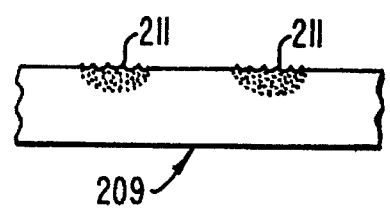

FIGS. 11A, 11B and 11C show three additional light pipe configurations for gathering light into the system with an increased effective field of view. In FIG. 11A, a light pipe 201 has a flat end roughened to form a diffuser thereacross. In FIG. 11B, an end of the light pipe 205 is generally shaped into a cone and the resulting conical surface roughened to increase the range of angles of rays which are accepted into the light pipe. The light pipe 209 of FIG. 11C has a number of roughened areas 211 along its length in order to allow entry into the light pipe from its side. If the light pipe 209 is shaped in a circle, square, triangle, or similar shape, in a plane perpendicular to the paper, then it becomes a two dimensional gatherer of light. This is very useful for viewing the heating lamps of a semiconductor furnace.

Figure 12:
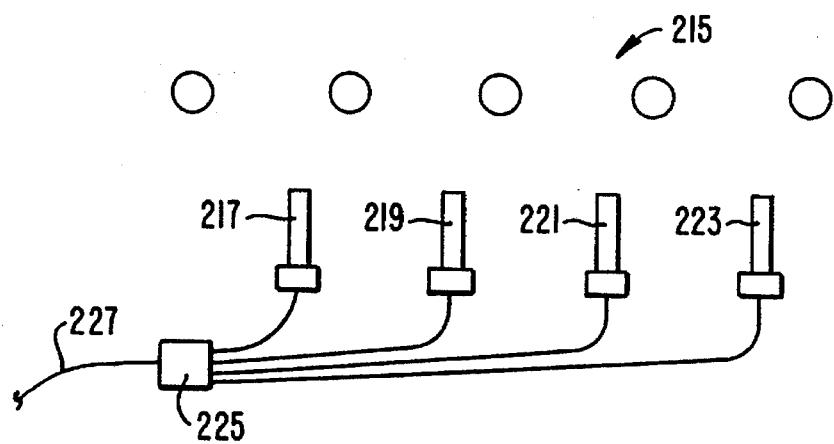
FIG. 12 illustrates another light gathering system that employs multiple light pipes.

With reference to FIG. 12, another technique for viewing a wide area of the lamps 215 is to use multiple light pipes, four such light pipes 217, 219, 221 and 223 being shown. The light pipes are most desirably arranged in a two-dimensional array (not shown) but the linear array illustrated in FIG. 12 is also useful. The optical signals from these light pipes are carried by their respective individual optical fibers to a coupler 225, where they are combined into a single optical signal in a single optical fiber 225. The signal from each light pipe may be attenuated in a way to provide a weighting factor to the contribution of each light pipe optical signal to the combined signal. The area of the lamps which contribute to the light being reflected from the wafer area being monitored can thus be gathered with the same relative intensity distribution that is incident upon that wafer area.

The embodiments of the invention described above can be altered, if desired, to employ lens elements in place of the illustrated light pipes to gather light from the lamps and the wafer onto respective photodetectors. Such lenses can also be used in conjunction with light pipes. However, direct use of light pipes made from high index of refraction material, as described, is preferred.

Figure 13:
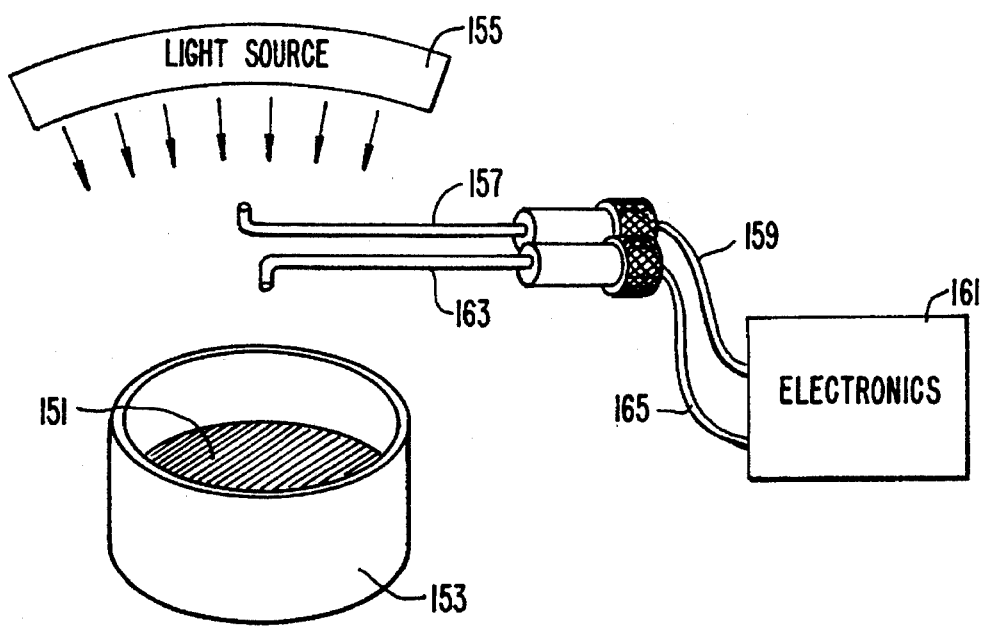
FIGS. 13 and 14 show two additional applications of the measuring techniques of the present invention.
Figure 14:
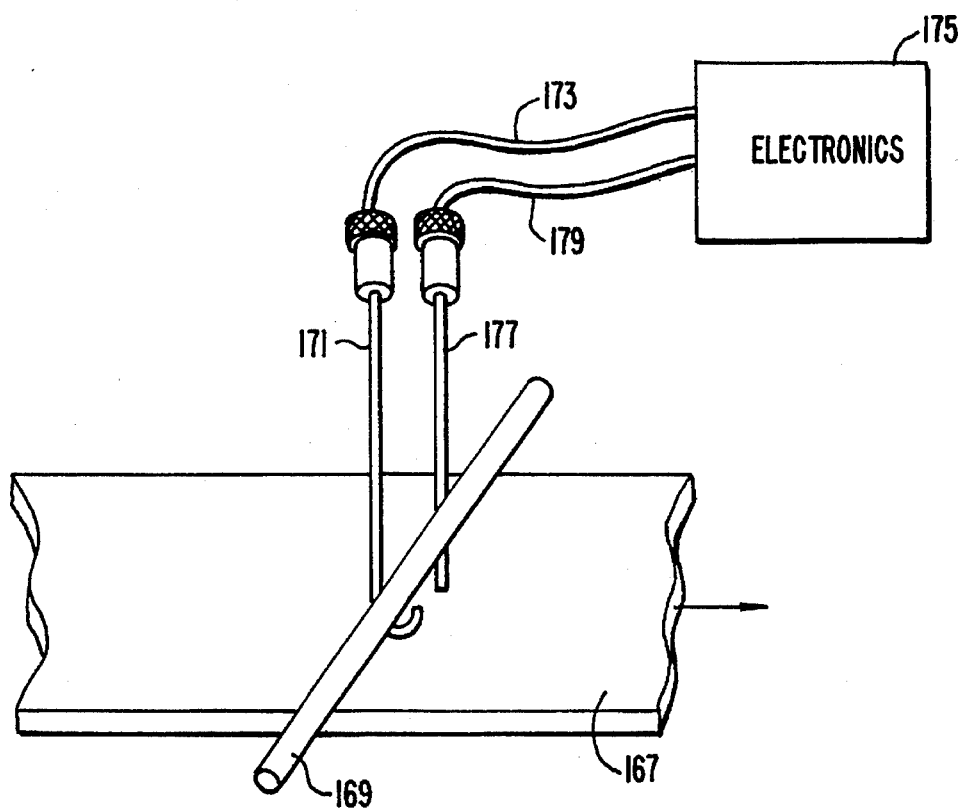

As stated previously, the techniques of the present invention are useful in many surface measurement applications other than semiconductor processing, both with surfaces that are being heated and those that are not. FIGS. 13 and 14 generally illustrate two such additional applications. In FIG. 13, a quantity of molten metal 151 is carried by a crucible 153. An incandescent or fluorescent light source 155 directs light against the surface of the metal bath 151 for the purpose of making a measurement of any of the physical, thermal or optical characteristics discussed above for that surface. The light source will usually not have a purpose of heating the metal bath 151 but could do so if desired. A light pipe 157 gathers some of the emission of the light source 155 and communicates it by way of an optical fiber to a measuring instrument 161 of the type described with respect to FIG. 3. Similarly, a light pipe 163 gathers some of the light that is reflected from the top surface of the molten metal 151 and communicates that light signal through an optical fiber 165 to the instrument 161.

The emissivity of the surface of the molten metal 151 is usually unknown, and further will generally be changing as a result of its processing. Oxidation is one such change. Another results from treatment of the surface by the addition of a film or layer of some other material. The measurement techniques of the present invention are particularly valuable in such difficult situations where conventional non-contact, optical techniques will not operate properly.

In FIG. 14, a moving sheet 167 of aluminum or other metal is moving past a surface characteristic measurement station. That measurement station includes a light source 169 positioned above the path of the sheet material 167. The source 169 is shown as a single standard fluorescent light tube but can be of some other form so long as its light output has the ripple intensity component discussed above. A light pipe 171 collects a portion of the source output and carries it by an optical fiber 173 to a measuring instrument 175. Another light pipe 177 carries a portion of that light, after reflection by the surface of the material 167, to the instrument 175 over another optical fiber 179. This system provides a real time measurement of any one of many characteristics of the material surface in a manner that allows processing of the metal 167 to be controlled, at least in part, by the measured results.

Indeed, the applications of the measuring techniques described herein are extremely broad, particularly where some ultimate characteristic of an object that is desired to be measured is related to the emissivity of a surface of that object. The Surface emissivity is measured by the techniques of the present invention and then converted to the desired characteristic on the basis of an empirically determined table, formula, or the like. This is the general process described above for measuring layer thicknesses.

Other characteristics which can be ascertained from a measurement of surface emissivity include an amount of grain growth or shrinkage, annealing, the formation of microscopic cracks or textural changes in a surface, a amount of diffusion of oxygen into a surface of material such as titanium nitride, migration of metal to a surface from material below that surface, the cure level of a polymer material, the amount of reflow of a metal, and the extent of delamination of two layers being held together. The process for measuring any such quantity follows that of FIG. 6 except that the calculation step 105 converts the averaged surface emissivity and temperature into one of these other quantities instead of film thickness. And, of course, the measurement is not performed within a semiconductor processing furnace but rather more like that illustrated in FIGS. 13 and 14. Further, such measurements may be used to control the process which is causing the determined characteristic to change in order that it will be allowed to proceed to a certain point and then be stopped.

Another application of the technique is in the detection of the endpoint of a semiconductor etch or photoresist development process. In this or other situations where a layer of material having a different surface emissivity than an underlying surface is being removed, either totally or partially, the emissivity suddenly changes upon breaking through the layer to expose the underlying surface. Such an endpoint detection can optionally be used to control termination of the etch or develop process.

Although the various aspects of the present invention have been described with respect to their preferred embodiments, it will be understood that the invention is entitled to protection within the full scope of the appended claims.

It is claimed:

1. A method of determining a characteristic of a layer of one material on a surface of another material, comprising the steps of:

directing continuous electromagnetic radiation toward the layer and surface in a manner to be modified thereby, said radiation including a given wavelength range and having a d.c. intensity level with a periodic a.c. intensity ripple superimposed thereon, detecting a combined level of the intensity within the given wavelength range of the directed electromagnetic radiation after being modified by the layer and the intensity of electromagnetic radiation within said wavelength range that is emitted by the layer and surface to thereby generate a first electrical signal having a first d.c. component with a periodic a.c. intensity ripple component of a first magnitude superimposed thereon, generating a second electrical signal corresponding to the directed electromagnetic radiation, said second electrical signal having a second d.c. component with a periodic a.c. ripple component of a second magnitude superimposed thereon, and determining the characteristic of the layer from at least the first and second magnitudes of the ripple components of the respective first and second electrical signals.

2. The method according to claim 1 wherein said surface includes a semiconductor material substrate, and wherein said given wavelength range lies below an absorption band edge of the semiconductor substrate.

3. The method according to claim 1 wherein said surface includes a metal undergoing heat treating.

4. The method according to claim 1 wherein at least one of the radiation detecting or signal generating steps includes the steps of gathering the electromagnetic radiation in a light pipe made of any one of quartz, sapphire or cubic zirconia, and directing the gathered radiation onto a photodetector.

5. The method according to claim 1 wherein the step of generating the second electrical signal includes gathering a portion of the electromagnetic radiation directed toward the layer and surface through a domed end of a light pipe, thereby to increase a field of view of the light pipe.

6. The method according to claim 1 wherein the determining step includes taking a ratio of the first and second periodic intensity ripple component magnitudes of said first and second signals.

7. The method according to claim 6 wherein the determining step includes the step of measuring the time varying component magnitudes by integrating the first and second signals with respect to respective mean values of said signals.

8. The method according to claim 6 wherein the determining step includes the further step of subtracting said ratio from one, thereby determining a quantity related to the emissivity of the layer and surface.

9. The method according to claim 8 wherein the determining step additionally includes multiplying said ratio by said second d.c. component and then arithmetically combining the result with said first d.c. component, thereby determining a quantity related to the temperature of the layer and surface.

10. The method according to claim 6 wherein the determining step includes the additional steps multiplying said ratio by said second d.c. component of the second signal and then arithmetically combining the result with said first d.c. component of the first signal, thereby determining a quantity related to the temperature of the layer and surface.

11. The method according to claim 6 wherein the determining step includes the additional steps of multiplying said ratio by the second signal and then subtracting the result from the first signal.

12. The method according to either of claims 1 or 6 wherein the characteristic being determined includes a thickness of the layer.

13. The method according to either of claims 1 or 6 wherein the characteristic being determined includes a composition of the layer.

14. The method according to claim 1 wherein the characteristic determining step is caused to occur simultaneously as the layer is being formed on the surface.

15. The method according to claim 14 which comprises an additional step of utilizing the layer characteristic determination to control a process of forming the layer on the surface.

16. The method according to either of claims 1 or 10 wherein the step of directing electromagnetic radiation toward the layer and surface includes use of heating lamps driven by a varying magnitude current, thereby to heat the layer and surface by such lamp illumination.

17. The method according to claim 1 wherein the radiation directing step includes positioning the surface in the path of illumination from ambient building incandescent or fluorescent lamps.

18. A non-contact method of determining a characteristic of a surface, comprising the steps directing against said surface incident electromagnetic radiation having a time varying component, wherein a portion of said incident radiation is reflected from said surface with such a time varying component, generating a first electrical signal corresponding to a combined level of said reflected portion of the incident electromagnetic radiation and electromagnetic radiation that is emitted from said surface, generating a second electrical signal corresponding to a level of the incident electromagnetic radiation that is being directed against said surface, determining a mean value of each of the first and second electrical signals, integrating each of the first and second electrical signals with respect to their respective mean values, thereby to provide a value of a time varying component in each of said first and second signals, and combining at least the time varying component values of said first and second signals in a manner to obtain said surface characteristic.

19. The method according to claim 18 wherein the combining step includes taking a ratio of the time varying component values of said first and second signals.

20. In a system for forming a layer of material on a substrate surface that is positioned within a chamber having a substantially optically transparent window in a wall thereof, wherein said substrate is heated by directing continuous wave electromagnetic radiation of a given bandwidth against said substrate through said window from outside of said chamber from an electromagnetic radiation source that is characterized by having a time varying intensity component, an improvement adapted to monitor formation of said layer, comprising:

a first photodetector that is characterized by generating an electrical signal proportional to a level of electromagnetic radiation incident thereon that includes said time varying intensity radiation component, means positioned with respect to the substrate surface for carrying to the first photodetector both a portion of source electromagnetic radiation after interaction with said substrate surface and electromagnetic radiation emitted by said substrate surface within the bandwidth of the source electromagnetic radiation, thereby to generate a first electrical signal that contains a first time varying component, means for generating a second electrical signal that contains a second time varying component corresponding to the time varying intensity component of the source of electromagnetic radiation and substantially without any component corresponding to the radiation emitted from the substrate surface, and means receiving said first and second electrical signals with their respective time varying components for determining a characteristic of the layer.

21. The system of claim 20 wherein said second electrical signal generating means includes a second photodetector positioned to receive a portion of the source electromagnetic radiation, said first and second photodetectors being positioned outside of said chamber, and said first and second photodetector radiation carrying means each include respective first and second light pipes that each have one end thereof positioned within said chamber.

22. The system of claim 21 wherein said first and second light pipes are made substantially entirely of either sapphire or cubic zirconia material.

23. The system of claim 21 wherein at least one of said first and second light pipes includes a solid end thereof that is convexly shaped and positioned to receive radiation therethrough.

24. A method of monitoring one of a physical and chemical characteristic of a material surface, comprising the steps of:
   directing electromagnetic radiation toward the surface in a manner to be modified thereby, said radiation including a given wavelength range and having a periodic intensity variation,
   detecting a level of the intensity of the given wavelength range of the electromagnetic radiation modified by the surface to thereby generate a first electrical signal having a periodic intensity variation of a first magnitude,
   generating a second electrical signal having a periodic intensity variation of a second magnitude that corresponds to the intensity of the electromagnetic radiation within said given wavelength range that is being directed toward the layer and surface,
   determining from at least the magnitudes of the periodic intensity variations of the first and second electrical signals a quantity related to an emissivity of the surface, and
   using said emissivity related quantity to determine one of a physical and chemical characteristic of the surface.

25. The method according to claim 24 wherein the determining step includes taking a ratio of the periodic intensity variation magnitudes of said first and second signals.

26. The method according to claim 25 wherein the determining step includes the further step of subtracting said ratio from one.

27. The method according to claim 24 wherein the determining step includes the step of measuring the periodic intensity variation magnitudes by integrating the first and second signals with respect to respective mean values of said signals.

28. The method according to claim 27 wherein the determining step includes the further steps of taking a ratio of the periodic intensity variation magnitudes of said first and second signals, and subtracting said ratio from one, thereby determining a quantity related to emissivity of the surface.

29. The method according to claim 24 wherein the using step includes converting the emissivity related quantity to a quantity related to one of growth and shrinkage of grains within the surface.

30. The method according to claim 24 wherein the using step includes converting the emissivity related quantity to a quantity related to the existence of microcracks or textural changes within the surface.

31. The method according to claim 24 wherein the using step includes converting the emissivity related quantity to a quantity related to an amount of gaseous material absorbed in the surface.

32. The method according to claim 24 wherein said surface includes polymer material and the using step includes converting the emissivity related quantity to a quantity related to the level of cure of said polymer material.

33. The method according to claim 24 wherein the surface is on a layer of material adhered to a substrate and the using step includes converting the emissivity related quantity to a quantity related to an amount of delamination of the material layer from the substrate.

34. The method according to any one of claims 1, 2 or 10, wherein the step of generating the second electrical signal includes detecting the intensity of the electromagnetic radiation within said given wavelength range that is being directed toward said layer and surface.

35. The method according to either of claims 1 or 6, wherein the characteristic determining step includes determining a physical characteristic of the layer.

36. The method according to either of claims 1 or 6, wherein the characteristic determining step includes determining a chemical characteristic of the layer.

37. The method according to either of claims 1 or 2, wherein the characteristic determining step includes determining a thermal characteristic of the layer.

38. The system according to claim 20 wherein said second electrical signal generating means includes a second photodetector and optics that couples electromagnetic radiation from the substrate heating source to said second photodetector.

39. The system according to claim 20 wherein said second electrical signal generating means includes means for causing said second electrical signal to be proportional to said source radiation portion that interacts with the substrate surface before reaching the first photodetector.

40. The system according to claim 20 wherein said layer characteristic determining means includes means for determining the thickness of the layer.

41. The system according to claim 20 wherein said layer characteristic determining means includes means for determining the chemical composition of the layer.

42. The system according to claim 20 wherein said layer characteristic determining means includes means for combining magnitudes of the first and second electrical signal time varying components.

43. The method according to claim 24 wherein said surface emits electromagnetic radiation within said given wavelength range, and wherein the step of generating a first electrical signal includes detecting a level of electromagnetic radiation within said given wavelength range that is emitted by said surface.

44. The method according to claim 24 wherein the step of generating the second electrical signal includes detecting the intensity of the electromagnetic radiation within said given wavelength range that is being directed toward said surface.

45. A non-contact method of measuring the temperature of a surface, comprising:
   directing continuous electromagnetic radiation toward the surface in a manner to be modified thereby, said radiation including a given wavelength range and having a d.c. intensity level with a periodic a.c. intensity ripple superimposed thereon,
   detecting a combined level within the given wavelength range of the directed electromagnetic radiation after being modified by the surface and of electromagnetic radiation emitted from the surface to thereby to generate a first electrical signal having a first d.c. component with a periodic a.c. intensity ripple component of a first characteristic superimposed thereon, generating a second electrical signal corresponding to the directed electromagnetic radiation, said second electrical signal having a second d.c. component with a periodic a.c. ripple component of a second characteristic superimposed thereon, and combining the first and second d.c. components with the first and second a.c. component characteristics in a manner to determine the temperature of the surface.

46. The method according to claim 45 wherein the first signal is an electrical signal generated by positioning a photodetector in a path of the electromagnetic radiation being directed toward the surface, said electrical signal being used to calculate the temperature of the surface.

47. A non-contact method of measuring the temperature of a surface, comprising:

directing electromagnetic radiation toward the surface in a manner to be modified thereby, said electromagnetic radiation including a repetitive time varying component, generating a first electrical signal corresponding to the magnitude over time of the electromagnetic radiation within a given wavelength range that is so directed, said first signal thereby having a repetitive time varying component, generating a second electrical signal corresponding to a common optical signal over time which includes electromagnetic radiation within said given wavelength range that is emitted from the surface and the directed electromagnetic radiation within said given wavelength range after being modified by the surface, said second electrical signal thereby also having a repetitive time varying component, and calculating the temperature of the surface from the first and second electrical signals, the calculation using relative characteristics of the repetitive time varying components of the first and second electrical signals.

48. The method according to claim 47 wherein the first signal is an electrical signal generated by positioning a photodetector in a path of the electromagnetic radiation being directed toward the surface, said electrical signal being used to calculate the temperature of the surface.

49. The method according to claim 47 wherein the electromagnetic radiation directed toward the surface is continuous with a d.c. component and the repetative time varying component includes an a.c. ripple superimposed thereon.

50. The method according to either of claims 45 or 47 wherein the emissivity of the surface is also calculated from the first and second electrical signals.

51. The method according to either of claims 45 or 47 wherein the electromagnetic radiation that is directed toward the surface originates from a lamp energized with alternating electrical current.

52. In a process of heating an object by directing electromagnetic radiation against at least one surface of the object from a plurality of lamps energized from a power source having a periodic magnitude variation, wherein an intensity of the radiation from the lamps includes a time varying component, a method of determining a characteristic of said object surface, comprising:

generating a first electrical signal corresponding to a combination of radiation emitted from said object surface and a part of the radiation from said lamps after interacting with the object surface, generating a second electrical signal corresponding to said part of the radiation from said lamps before interacting with the object surface, and determining said object surface characteristic from said first and second signals.

53. The method according to claim 52 wherein the second signal is generated by optically directing a portion of the intensity of said part of the radiation from the lamps onto a photodetector, whereby an output of said photodetector is said second signal.

54. The method according to claim 52 wherein the second signal is generated by individually gathering a portion of the radiation from at least some of the lamps and then combining the individually gathered lamp radiation with relative weights according to the individual contributions of said at least some of the lamps to said lamp radiation part.

55. The method according to claim 52 wherein the first signal is generated from a radiation combination that includes said part of the radiation from the lamps after being reflected from the object surface.

56. The method according to claim 52 wherein said part of the radiation of the lamps is a given spatial extent of the plurality of lamps, whereby said first and second signals both include lamp radiation from said given spatial extent.

* * * * *

UNITED STATES PATENT AND TRADEMARK OFFICE
CERTIFICATE OF CORRECTION

PATENT NO. : 5,490,728
DATED : February 13, 1996
INVENTOR(S) : Charles W. Schietinger et al.

It is certified that error appears in the above-indentified patent and that said Letters Patent is hereby corrected as shown below:

On the title page:

Section [60] Related U.S. Application Data, line 6, replace:
    "Apr. 29, 1991, which is a continuation-in-part of Ser. No."
with
    --Apr. 27, 1992, which is a continuation-in-part of Ser. No.--

In Column 17 at line 50 in Claim 10, replace:
    "mining step includes the additional steps multiplying said"
with
    --mining step includes the additional steps of multiplying said--

In Column 18 at Line 14 in Claim 18, replace:
    "Of a surface, comprising the steps"
with
    --Of a surface, comprising the steps of:--

Signed and Sealed this

Sixth Day of January, 1998

Attest:

BRUCE LEHMAN

Attesting Officer    Commissioner of Patents and Trademarks